United States Patent [19]

Hag et al.

[11] Patent Number: 4,474,993
[45] Date of Patent: Oct. 2, 1984

[54] METHOD FOR THE HYDROLYSIS OF α-CHLORINATED TOLUENE COMPOUNDS

[76] Inventors: Göran L. F. Hag, Tvetgatan 197, S-442 33 Kungälv, Sweden; Risto K. Rantala, Andelslagsvägen 41B B2, SF-00660 Helsingfors 66, Finland

[21] Appl. No.: 372,458

[22] Filed: Apr. 28, 1982

[30] Foreign Application Priority Data

May 4, 1981 [SE] Sweden ................................. 8102761

[51] Int. Cl.$^3$ ..................... C07C 45/43; C07C 29/124
[52] U.S. Cl. .................................... 568/437; 568/812; 568/715; 422/256
[58] Field of Search ....................... 568/715, 437, 812; 562/493

[56] References Cited

U.S. PATENT DOCUMENTS 2,796,443  6/1957  Meyer et al. ........................ 568/715
3,557,222  1/1971  Withers et al. ..................... 568/715

Primary Examiner—Bernard Helfin
Attorney, Agent, or Firm—Luedeka & Neely

[57] ABSTRACT

The disclosure relates to a continuous method and an apparatus for the hydrolysis of α-chlorinated toluene compounds, preferably benzyl chloride. The hydrolysis, which takes place in a hydrolysis zone, is characterized by being conducted in countercurrent between the aqueous phase containing the hydrolyzing agent and the organic phase containing the α-chlorinated toluene compound and an inert organic solvent, such as toluene. After the hydrolysis, the organic phase is washed with water in a washing zone, while the aqueous phase is extracted with inert solvent in an extraction zone. The resulting product of hydrolysis, preferably benzyl alcohol, is thereafter separated from the organic phase by distillation, suitably in two stages, by means of two distillation columns connected in series.

9 Claims, 3 Drawing Figures

METHOD FOR THE HYDROLYSIS OF α-CHLORINATED TOLUENE COMPOUNDS

The present invention relates to a method and an apparatus for the hydrolysis of α-chlorinated toluene compounds and more particularly to a method in which the α-chlorinated toluene compound is hydrolyzed with an aqueous solution of a hydrolyzing agent in an at least stoichiometric amount in the presence of an inert organic solvent, whereupon the resulting product of hydrolysis is recovered.

The expression "α-chlorinated toluene compounds" herein refers to α-chlorinated toluenes and toluene derivatives of the general formula

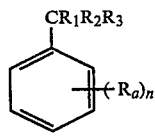

wherein at least one of $R_1$, $R_2$ and $R_3$ is Cl and wherein $(R_a)_n$ designates that the benzene nucleus may have one or more substituents which may be same or different and are selected from the group consisting of H, Cl, Br and $—C_mH_{2m+1}$, n being 0 or an integer of 1–5, and m being an integer, preferably of 1–6. Preferably, the α-chlorinated toluene compounds are selected from the α-chlorinated toluenes exemplified below, viz. benzyl chloride, $C_6H_5CH_2Cl$, or benzal chloride, $C_6H_5CHCl_2$, which by hydrolysis are converted to benzyl alcohol, $C_6H_5CH_2OH$, and benzaldehyde, $C_6H_5CHO$, respectively. The most preferred embodiment of the invention relates to the hydrolysis of benzyl chloride to benzyl alcohol, and for reasons of simplicity the invention will be described below merely with reference thereto. It should however be pointed out that the invention also comprises and is applicable to the hydrolysis of benzal chloride and other α-chlorinated toluene compounds without the need for a particular description thereof.

At room temperature, benzyl alcohol is a colourless liquid having a density of 1.042–1.047 g/cm$^3$ and a boiling point of 206° C. In alcohol and ether, benzyl alcohol is readily soluble, whereas in water it is only soluble in the proportion of 4:100 at 25° C. Benzyl alcohol has a wide range of application and is used for instance within the photographic industry, the cosmetics industry, the pharmaceutical industry, the textile industry, and the dye and lacquer industry.

For most applications, it is required that the benzyl alcohol is pure and free of impurities, in particular chlorinated ones. This is an actual problem because benzyl alcohol is usually prepared by alkaline hydrolysis of benzyl chloride, which means a source of such impurities. In order to avoid this problem, the hydrolysis is normally allowed to proceed to such completion that residues of unconverted benzyl chloride are eliminated. In batchwise hydrolysis of benzyl chloride, this will give hydrolysis times of up to 20–30 h or more. It is obvious to anyone that processing times of such lengths are uneconomical. A further problem is the formation of the undesired by-product dibenzyl ether. The extent of dibenzyl ether formation may vary from about 0.5 to 30% by weight of the final product and is affected by a number of factors such as choice of hydrolyzing agent, temperature, concentration of hydrolyzing agent, and use of inert solvent. Thus, for instance, the use of sodium carbonate as hydrolyzing agent will give rise to a lower relative rate of formation of dibenzyl ether as compared with sodium hydroxide. Furthermore, a higher concentration of hydrolyzing agent generally gives rise to a higher relative rate of formation of dibenzyl ether. The addition of inert solvent, such as toluene, to the benzyl chloride entails a substantial reduction in the formation of dibenzyl ether. Further, a raised hydrolysis temperature will increase the production of dibenzyl ether.

In addition, dibenzyl ether has a tendency at higher temperatures to decompose thermally into benzaldehyde and toluene. This means that in the preparation of dibenzyl ether-free benzyl alcohol, distillation must be conducted under vacuum and further, in order to sufficiently lower the bottom temperature in the distillation, the bottom product must contain up to 50% of benzyl alcohol, i.e. a considerable portion of the benzyl alcohol will be lost. This further emphasizes the importance of minimizing the formation of dibenzyl ether.

Another problem encountered in connection with the production of benzyl alcohol by the hydrolysis of benzyl chloride is that the heterogeneous mixture of benzyl chloride and the alkaline aqueous solution of the hydrolyzing agent is highly corrosive. This property increases with increasing temperature, which causes serious materials problems.

Yet another problem in this context is to bring about, after the hydrolysis, a satisfactory physical separation between the organic benzyl alcohol phase and the spent alkaline aqueous solution of the hydrolyzing agent. This causes difficulties, because the density of benzyl alcohol almost equals that of the spent hydrolyzing agent solution, this giving an additional loss of benzyl alcohol in that benzyl alcohol will be entrained by the aqueous phase owing to difficulties of separation.

A similar problem also to be considered in this context is the mutual solubility of the organic benzyl alcohol phase and the aqueous phase. At 20° C., the solubility of water in pure benzyl alcohol is 4.9% by weight and the solubility of benzyl alcohol in pure water is 3.9% by weight. It is true that the solubility of benzyl alcohol is reduced if the water contains dissolved sodium chloride, but at 18° C., for instance, the solubility of a 15.7% by weight sodium chloride solution still is 1% by weight. This means a considerable loss of benzyl alcohol to the aqueous phase. This loss normally amounts to about 3–5% by weight, calculated on the total amount of benzyl alcohol. The solubility of water in benzyl alcohol is not affected by the degree of salinity, which means that if one wishes to produce benzyl alcohol of a purity of more than about 96%, water must be distilled off from the raw product.

It will be appreciated from the above that the production of benzyl alcohol by the hydrolysis of benzyl chloride is linked with various problems making it more difficult to prepare, in as short a hydrolysis time as possible, a benzyl alcohol product of the highest possible purity, i.e. a product which to the greatest extent possible is free of both unconverted benzyl chloride and dibenzyl ether.

An attempt at overcoming the above-discussed problems is disclosed in U.S. patent specification No. 3,557,222. This patent specification relates to the continuous hydrolysis of benzyl chloride, the basic feature being that the hydrolysis is conducted in a tubular concurrent reactor under turbulent flow of the reactants in the hydrolysis zone. In order to reduce the formation of dibenzyl ether, it is preferred that the benzyl chloride is mixed with an inert solvent, such as toluene, for the benzyl chloride and the resulting benzyl alcohol product. The hydrolysis reaction is conducted at a temperature of about 150°–350° C., 180°–275° C. being particularly preferred. The pressure should be sufficient to maintain the reactants in the liquid phase.

Although the continuous method according to U.S. patent specification No. 3,557,222 is an improvement in relation to the earlier used batchwise process, the continuous method according to said patent specification nevertheless suffers from several drawbacks.

Thus, the hydrolysis reaction is conducted in a concurrent reactor, this requiring a relatively large reactor volume and a particular separator after the concurrent reactor. Further, the concurrent reaction demands a relatively large excess of hydrolyzing agent. Another drawback is the high temperature which in actual practice is required in the process disclosed in the patent specification. At the indicated preferred temperatures of 180°–275° C., and in particular above 220° C., there is most often required a particular heating system, using e.g. hot oil, which increases costs. As will have been evident from the above, the high temperatures in addition cause serious materials problems on account of the corrosive nature of the reaction mixture and, moreover, the formation of the undesired by-product dibenzyl ether increases at high temperatures. Elevated temperatures of course also entail an increase in energy consumption. The pressure, which as stated above should be sufficient to maintain the reactants in the liquid phase, also increases at raised temperatures, which in turn results in demands on thicker material in tubes and reactor, as well as in a greater risk of leakage.

The object of the present invention is to alleviate or eliminate the problems of the prior art technique and provide a continuous method for rapidly and completely hydrolyzing α-chlorinated toluene compounds, such as benzyl chloride, to corresponding high-grade alcohols, such as benzyl alcohol, with minimum formation of dibenzyl ether and minimum loss of produced alcohol.

Briefly, this object is achieved according to the invention by conducting the hydrolysis in countercurrent in the presence of an inert organic solvent, the spent hydrolysis solution being then extracted in countercurrent with inert solvent, while the organic phase, after the hydrolysis, is washed in countercurrent and is treated for separation of produced alcohol.

More particularly, the invention provides a method for the hydrolysis of an α-chlorinated toluene compound, in which the α-chlorinated toluene compound is hydrolyzed with an aqueous solution of a hydrolyzing agent in an at least stoichiometric amount in the presence of an inert organic solvent, whereupon the resulting product of hydrolysis is recovered, the method being characterized by conducting the hydrolysis reaction in countercurrent, an organic phase, containing said α-chlorinated toluene compound and said inert solvent, flowing in a hydrolysis zone countercurrently to an aqueous phase containing said aqueous solution of said hydrolyzing agent, and extracting said aqueous phase, after passing said hydrolysis zone, with an inert organic solvent in an extraction zone, while washing said organic phase, after passing said hydrolysis zone, with water in a washing zone, and thereafter separating and recovering the resulting product of hydrolysis from said organic phase.

According to the invention, there is also provided an apparatus for the hydrolysis of an α-chlorinated toluene compound, in which hydrolysis an organic phase containing the α-chlorinated toluene compound and an inert organic solvent is contacted with an aqueous phase containing an aqueous solution of a hydrolyzing agent in an at least stoichiometric amount, the apparatus being characterized in that it is arranged for countercurrent flow of the organic phase and the aqueous phase, and comprises a hydrolysis zone which at one end has an inlet for the α-chlorinated toluene compound and for inert solvent for the organic phase and an outlet for spent aqueous phase, and is connected to an extraction zone and which at the other end has an inlet for hydrolyzing agent and for water for the aqueous phase and an outlet for the organic phase containing the resulting product of hydrolysis, and is connected to a washing zone, said extraction zone at its distal end with respect to said hydrolysis zone having an inlet for inert organic solvent and an outlet for extracted and spent aqueous phase from the hydrolysis zone, and said washing zone at its distal end with respect to the hydrolysis zone having an inlet for water and an outlet for washed organic phase from the hydrolysis zone, and that the outlet from the washing zone is connected to separator means for separating the resulting product of hydrolysis from the organic phase.

The additional features of the invention will be apparent from the sub-claims.

The essential and characteristic feature of the invention, i.e. that the hydrolysis reaction between the α-chlorinated toluene compound in the organic phase and the hydrolyzing agent in the aqueous phase is conducted in countercurrent, yields several substantial advantages. Thus, a countercurrent reactor is in terms of capacity and volume the most advantageous reactor type permitting the use of a reactor of moderate volume as well as reduced reactor temperatures and pressure, thus making it possible to master problems dependent upon temperature and pressure conditions, such as materials problems and the like. By using a countercurrent reactor, there is no need of a particular separator after the reactor and, further, a smaller amount of hydrolyzing agent is required as compared with concurrent hydrolysis.

Another distinctive feature of the invention that contributes to making it possible to use a countercurrent reactor is the utilization of inert solvent. The use of an inert solvent is necessary to obtain a stable and sufficiently great difference in density between the (lighter) organic phase and the (heavier) aqueous phase, whereby the separation of the organic phase and the aqueous phase is facilitated, and the solubility of the benzyl alcohol in the aqueous phase is reduced as is the solubility of the water in the organic phase. It is also of great importance that the formation of dibenzyl ether is reduced to a low level.

Before a detailed description of the method and the apparatus according to the invention is made hereinbelow, the used components and the conditions of the method will first be briefly accounted for.

As mentioned by way of introduction, the α-chlorinated toluene compound to be hydrolyzed is preferably selected from benzyl chloride or benzal chloride. Benzyl chloride is a corrosive water-insoluble colourless liquid having a density of about 1.103 g/cm$^3$ and a boiling point of about 180° C. Benzal chloride is also a water-insoluble colourless liquid having a density of about 1.30 g/cm² and a boiling point of 207° C.

According to the invention, the other component in the organic phase is the inert solvent. It should serve as a solvent both for the starting compound to be hydrolyzed, for instance benzyl chloride, and for the resulting product of hydrolysis, for instance benzyl alcohol. As examples of suitable inert solvents, mention may be made of aromatic hydrocarbon solvents, such as benzene, xylene, toluene, ethyl benzene, or mixtures thereof. Toluene is particularly preferred as the inert solvent of the invention. The content of the inert solvent is generally within the range of 0.5–2, preferably about 0.8–1.2 parts by weight of solvent for 1 part by weight of α-chlorinated toluene compound according to the invention.

As hydrolyzing agent, use is made in the invention preferably of hydroxides, hydrogen carbonates or carbonates of alkali metals or alkaline earth metals. Of these, the most preferred are sodium hydroxide, sodium hydrogen carbonate or sodium carbonate, and in particular the latter two which reduce the formation of dibenzyl ether. The invention is however not restricted to these hydrolyzing agents, but other suitable hydrolyzing agents may also be employed.

The concentration of hydrolyzing agent in the aqueous phase may vary depending on for instance the particular hydrolyzing agent used, but generally is within the range of about 2–20% by weight, preferably about 5–15% by weight of the aqueous phase. The influence of the hydrolyzing agent on the formation of dibenzyl ether and its concentration have been mentioned above.

The ratio between the aqueous phase and the organic phase may vary within wide limits according to the invention and depend on the concentration of the hydrolyzing solution used and the stoichiometric excess of the hydrolyzing agent. Generally, this ratio or the relative flow in the hydrolysis zone of the aqueous phase with respect to the organic phase is within the range of 1:15 to 3:5, and preferably is about 1:5.

In the invention, the general principle is that the amount of hydrolyzing agent in the hydrolysis should be at least equal to the stoichiometrically required amount that is necessary for the hydrolysis of the benzyl chloride, and usually is up to double the stoichiometrically required amount. It is preferred to add the hydrolyzing agent in an excess of about 5–25% of the stoichiometrically required amount.

The temperature in the countercurrent hydrolysis according to the invention generally is within the range of 10°–300° C. and preferably within the range of 100°–180° C., a temperature of 120°–150° C. being particularly preferred.

The pressure should be sufficiently high to maintain the components in the hydrolysis process in the liquid state, and in the use of hydrogen carbonate or carbonate as hydrolyzing agent the pressure is maintained high in order to minimize the volume of carbon dioxide produced in the hydrolysis. Generally, the pressure is within the range of from atmospheric pressure to about 60 atmospheres (gauge pressure), preferably about 1–20 atmospheres (gauge pressure).

The reaction period or residence time in the countercurrent reactor for complete hydrolysis according to the method of the invention varies depending on the composition of the aqueous phase, such as concentration and type of hydrolyzing agent, and on the temperature in the hydrolysis zone. By the efficiency of the countercurrent reaction, the reaction period is however minimized and at a temperature of 180° C. is about 1–3 min.

The efficiency of the hydrolysis method according to the invention will appear from the high yield obtained. Generally, the yield of benzyl alcohol exceeds 99% of the theoretical yield while the proportion of unreacted benzyl chloride is less than 0.5% and the proportion of dibenzyl ether is less than 0.3%.

In the foregoing, the general aspects and conditions of the invention have been recited. In the following, the invention will be described in greater detail with reference to the accompanying drawings, in which.

Figure 1:
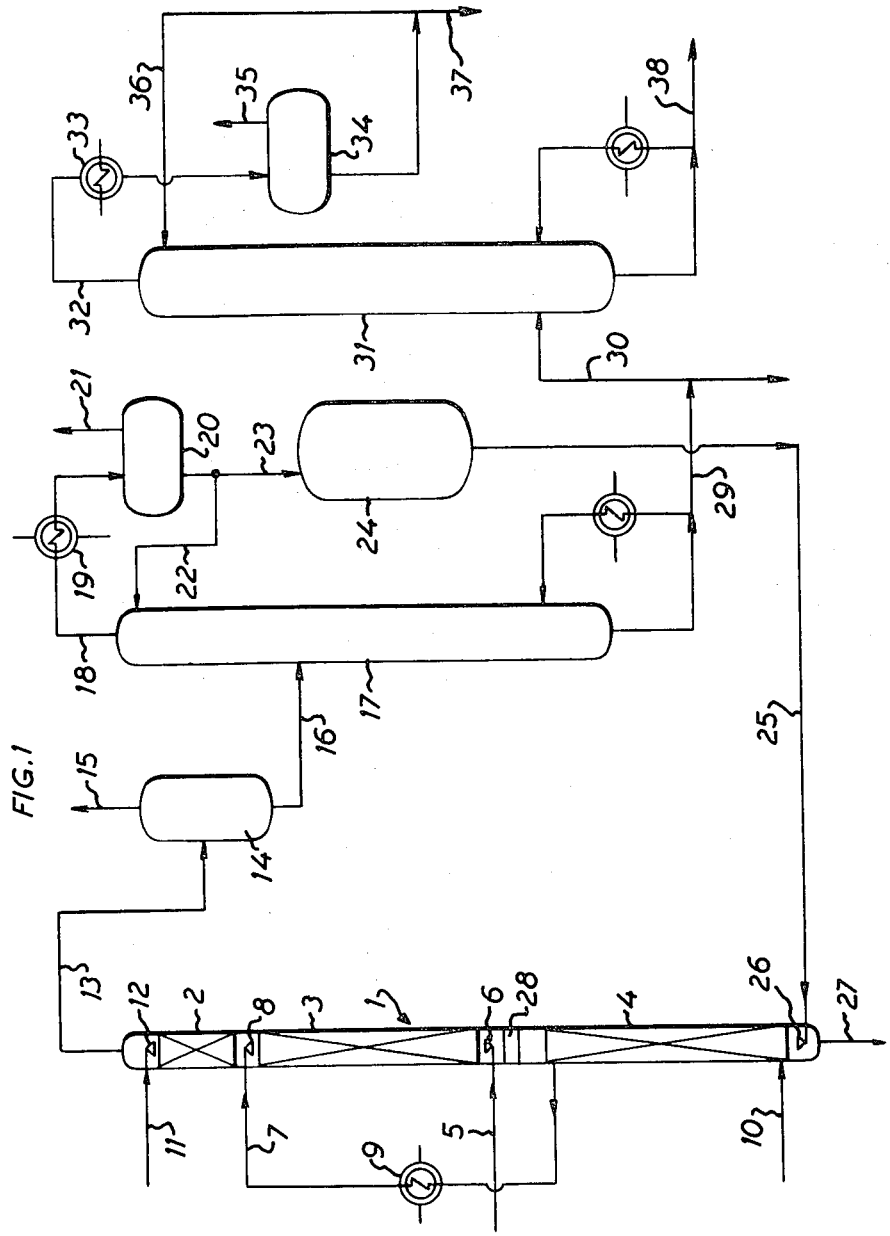
FIG. 1 is a diagram of a preferred embodiment of an apparatus for conducting hydrolysis according to the invention.

The apparatus shown in FIG. 1 comprises a reactor column 1 consisting of three sections, namely a washing zone 2, a hydrolysis zone 3, and an extraction zone 4. The benzyl chloride to be hydrolyzed is fed through a conduit 5 at the lower end of the hydrolysis zone where it is supplied through distributing nozzles 6 and is mixed with an inert solvent (toluene) which flows upwardly from the extraction zone. The benzyl chloride and the toluene together form a continuous organic phase which passes up through the hydrolysis zone 3 to meet a countercurrent flow of finely divided droplets of an aqueous phase which consists of an aqueous solution of hydrolyzing agent, such as sodium carbonate. The aqueous phase is formed partly from a stream of finely divided water droplets coming from the washing zone 2, and partly from a hydrolyzing agent solution which is charged through a conduit 7 to the upper part of the hydrolysis zone where the solution is supplied through a distributor means 8. In order to bring about the desired hydrolysis temperature, the hydrolyzing agent solution, before being introduced into the hydrolysis zone, is preheated by means of a heat exchanger 9 which uses for instance steam as heat exchange medium, and by heat exchange with the leaving spent hydrolyzing agent solution. The latter heat exchange is brought about in that the hydrolyzing agent is introduced through a conduit 10 to the lower part of the extraction zone and, after passing outside in surrounding relationship to the extraction zone, is evacuated therefrom at its upper end through the conduit 7. The arrangement of this heat exchange will appear more clearly from FIG. 2 and will be described in greater detail with reference thereto.

After completion of the hydrolysis in the hydrolysis zone, the organic phase ascends further through the washing zone 2 where it will meet a countercurrent flow of finely divided water droplets obtained by supplying cold water to the upper part of the washing zone through a conduit 11 and distributing nozzles 12. By the countercurrent flow in the washing zone, the organic phase will be cooled and washed and freed from water-soluble impurities, such as residues of hydrolyzing agent. By the cooling, the water content of the organic phase will also be reduced.

From the washing zone the cooled organic phase will pass through a conduit 13 to reach a collecting tank 14 in which the pressure is lowered to atmospheric pressure and any gases present, such as carbon dioxide, are vented to the atmosphere through a conduit 15.

From the collecting tank 14 the organic phase is passed on for separation and recovery of the produced benzyl alcohol. This is effected in a per se known manner in a distilling installation which preferably comprises two distillation columns.

The organic phase from the collecting tank 14 is passed through a conduit 16 to a distillation column 17 in which the organic phase is distilled under reduced pressure and the inert solvent (for instance toluene) leaves together with any unreacted benzyl chloride as top fraction through a conduit 18, is condensed by means of a cooler 19, collected in a tank 20 communicating by a conduit 21 with a vacuum system, and is drained from the tank 20, a partial flow being recycled by a conduit 22 to the distillation column 17 while another partial flow is passed by a conduit 23 to a storage tank 24 for inert solvent (for instance toluene).

From the storage tank 24 the inert solvent is recycled to the reactor column 1 through a conduit 25 and more precisely to the lower part of the extraction zone 4 where it is charged as finely divided liquid droplets by means of distributing nozzles 26.

After completed hydrolysis in the hydrolysis zone 3, the aqueous phase flows to the opposite, upper end of the extraction zone. Thus, in the extraction zone 4 the lighter inert solvent will rise countercurrently to the heavier aqueous phase which contains the spent hydrolyzing agent (substantially sodium chloride and excess of hydrolyzing agent). As a result of the contact with the inert solvent, benzyl alcohol dissolved in and accompanying the aqueous phase is extracted. The benzyl alcohol is thus recovered, whereby the yield is enhanced as at the same time the spent hydrolyzing agent solution is purified from organic material and can be safely disposed of through the drain 27.

In the extraction zone, the aqueous phase constitutes the continuous phase whereas the finely divided droplets of the inert solvent constitute the disperse phase. This relationship between the aqueous phase and the organic phase is opposite to that prevailing in the hydrolysis and washing zones. The transition from continuous aqueous phase to continuous organic phase takes place between the extraction zone and the hydrolysis zone and is facilitated by a particular coalescence mat 28 which may consist of a woven or knitted wire net.

Apart from the top fraction of inert solvent, there is also withdrawn from the distillation column 17 through the conduit 29 a bottom fraction which consists of substantially pure benzyl alcohol. This bottom fraction which may be called "First Product" contains in the case where sodium hydrogen carbonate or sodium carbonate is used as hydrolyzing agent at least 99.0% by weight of benzyl alcohol, at most 0.003% by weight of total chlorine, at most 0.04% by weight of benzaldehyde, and at most 0.90% by weight of dibenzyl ether. Depending on the demands in regard of quality and purity that are placed on the benzyl alcohol product, it may either be used directly or be further purified. In the latter case, the bottom fraction designated "First Product" is passed from the distillation column 17 through a conduit 30 to a second distillation column 31. The purpose of the second distillation is primarily to purify the benzyl alcohol from dibenzyl ether contained therein. In the second distillation which, like the first, occurs at a reduced pressure, benzyl alcohol is withdrawn as top fraction and dibenzyl ether as bottom fraction. As appears more clearly from FIG. 1, the top fraction is withdrawn through a conduit 32, condensed by means of a cooler 33 and is collected in a tank 34 communicating by a conduit 35 with a vacuum system, whereupon a partial flow is recycled to the distillation column through conduit 36 while another partial flow is withdrawn through conduit 37 as final product or "Second Product" consisting of highly pure benzyl alcohol. Generally, this "Second Product" contains at least 99.8% by weight of benzyl alcohol, at most 0.003% by weight of total chlorine, at most 0.04% by weight of benzaldehyde, and at most 0.01% by weight of dibenzyl ether.

The bottom fraction of dibenzyl ether leaves through a conduit 38.

Figure 2:
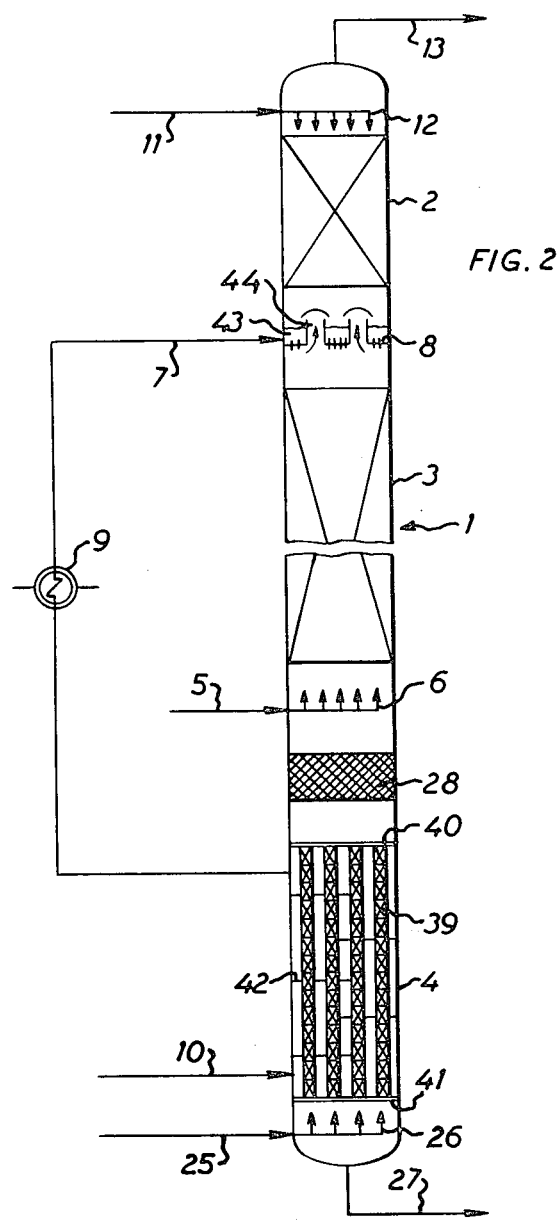
FIG. 2 is a schematic sectional view of the reactor column in FIG. 1.

In FIG. 2, the reaction column 1 of FIG. 1 is shown in greater detail, equivalent components having the same reference numerals as in FIG. 1. As appears from FIG. 2, the extraction zone 4 consists of a number of tubes 39 extending between an upper end wall 40 and a lower end wall 41. The tubes 39 are provided with packings in order further to improve the contact between the inert solvent which is ascending through the tubes, and the aqueous phase which is descending therethrough. As earlier intimated in connection with FIG. 1, the hydrolyzing agent solution is heated by heat exchange with the spent hydrolyzing agent solution in the extraction zone. As clearly appears from FIG. 2, this is effected by charging the fresh cold hydrolyzing agent solution to the lower part of the extraction zone through a conduit 10, whereupon the hydrolyzing agent solution when flowing over the tubes 39 is heated to finally leave through the conduit 7 at the upper part of the extraction zone. In order further to promote the heat exchange, the hydrolyzing agent solution is caused, by means of baffles 42, to follow a serpentine path through the extraction zone.

From FIG. 2 also appears the preferred embodiment of the distributor means 8 for finely dividing the hydrolyzing agent solution supplied to the hydrolysis zone. The distributor means consists of a perforated bottom of the "Chimney Tray" type whose bottom surface carries a water layer 43 formed of the hydrolyzing agent solution from the conduit 7 and the water from the washing zone 2. The water layer 43 flows through the perforations in the bottom to form fine droplets on its underside. The organic phase ascending from the hydrolysis zone is passed through the distributor means 8 in "chimneys" 44 which open above the water layer 43.

The other components in FIG. 2 have been described earlier in connection with FIG. 1 and, therefore, need no further explanation here.

Figure 3:
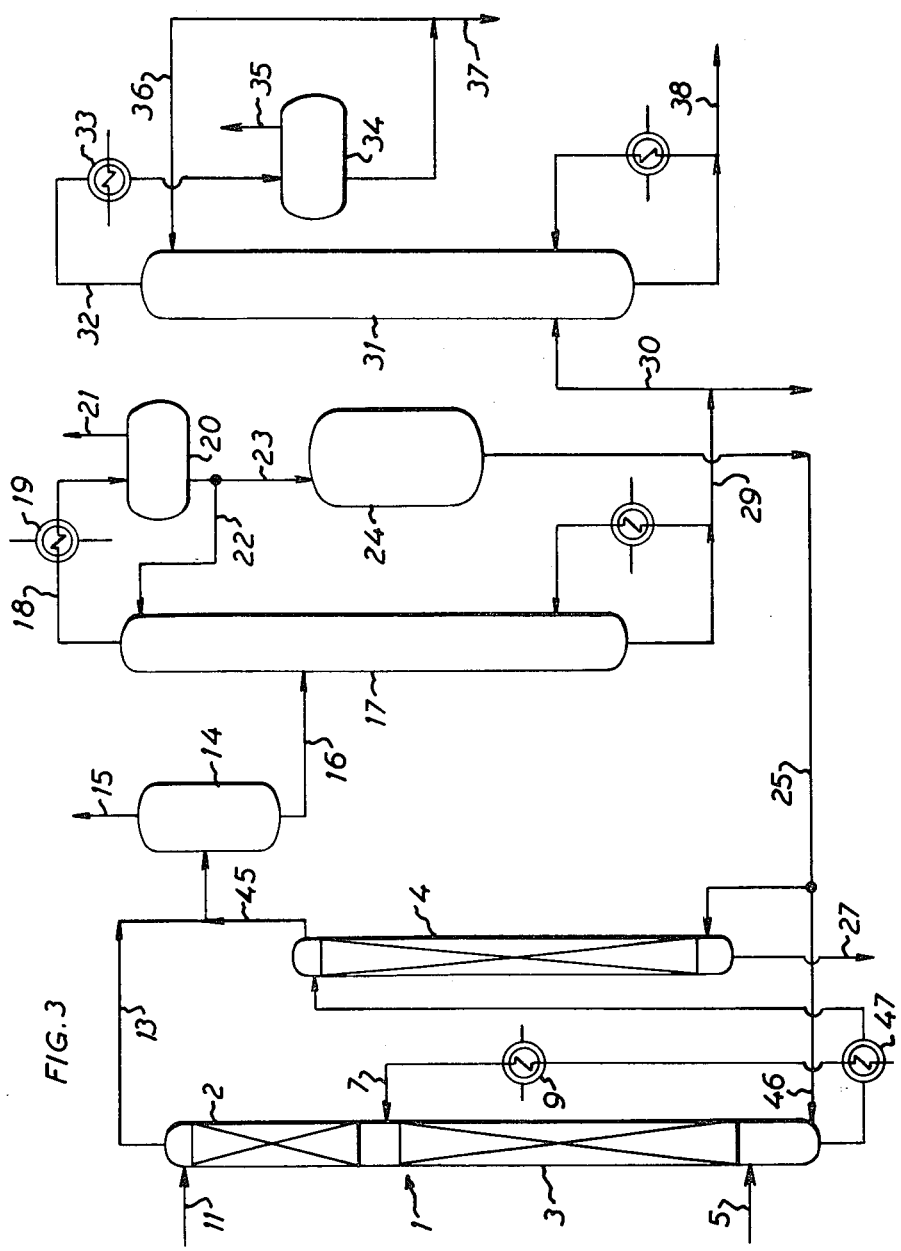
FIG. 3 is an alternative embodiment of the apparatus of FIG. 1.

In FIG. 3, there is shown an alternative embodiment of the apparatus according to the invention, components corresponding to those in FIG. 1 having the same reference numerals. The apparatus according to FIG. 3 differs from that in FIG. 1 only in that the reactor column 1 has been divided into two columns, the washing zone 2 and the hydrolysis zone 3 being arranged in one column while the extraction zone 4 is arranged in a separate column. As in FIG. 1, the inert solvent is passed through a conduit 25 to the lower part of the extraction zone 4. As opposed to the apparatus of FIG. 1, the inert solvent after passing the extraction zone is however not supplied to the hydrolysis zone but is diverted by a conduit 45 to the collecting tank 14 where it joins the organic phase from the washing zone. The hydrolysis zone instead receives inert solvent directly from the conduit 25 by a branch line 46. In FIG. 3, it is further intimated that the preheating of the hydrolyzing agent solution by heat exchange with the spent hydrolyzing agent solution is effected in a separate heat exchanger 47, but it is understood that this heat exchange may as well be effected in the manner described in connection with FIGS. 1 and 2. To further illustrate the invention, some non-limitative Examples thereof are given below.

EXAMPLES 1–5

These Examples relate to the preparation of benzyl alcohol by the hydrolysis of benzyl chloride by means of the apparatus according to FIG. 1. Test conditions and results will appear from Table 1.

The benzyl alcohol (First Product) obtained from the first distillation column, in all Examples except Example 4, had the following composition:

| Benzyl alcohol | at least 99.0% by weight |
|---|---|
| Total chlorine content | at most 0.003% by weight |
| (as chlorine) | |
| Benzaldehyde | at most 0.04% by weight |
| Dibenzyl ether | at most 0.90% by weight |

The benzyl alcohol (Second Product) obtained from the second distillation column, in all Examples, had the following composition:

| Benzyl alcohol | at least 99.8% by weight |
|---|---|
| Total chlorine content | at most 0.003% by weight |
| (as chlorine) | |
| Benzaldehyde | at most 0.03% by weight |
| Dibenzyl ether | at most 0.01% by weight |

This corresponds to reagent grade.

In the Examples, raw material consumption per kg of prepared product, i.e. benzyl alcohol, was also determined. The values in this respect for First Product and Second Product will appear from Table 2.

Further, energy consumption per kg of prepared product (benzyl alcohol) in the method of the invention was determined for both First Product and Second Product. The values in this respect are given in Table 3, where it should be noted that the energy consumption for pumping has not been included since it is negligible.

From Table 3, it appears that the method according to the invention produces benzyl alcohol with low energy consumption and, hence, is economical.

EXAMPLES 6–7

The procedure was the same as in Examples 1–5, with the difference however that p-xylene was used as inert solvent instead of toluene. Test conditions and test results appear from Table 4 showing that p-xylene can be used most advantageously as inert solvent in the invention. Tables 5 and 6 indicate raw material consumption and energy consumption per kg of prepared product.

EXAMPLES 8–9

These Examples relate to the preparation of benzaldehyde by the hydrolysis of benzal chloride by means of the apparatus according to FIG. 1. Test conditions and test results will appear from Table 7. It should here be noted that, since dibenzyl ether is not produced in the hydrolysis of benzal chloride, Table 7 has no column for dibenzyl ether.

TABLE 1

| Ex. No. | Benzyl chloride (kg/h) | Benzyl chloride (kmol/h) | Toluene (kg/h) | Hydrolyzing agent Type | Hydrolyzing agent Amount (kg/h) | Hydrolyzing agent Amount (kmol/h) | Hydrolyzing agent Molar excess (%) | Hydrolyzing agent Concentration (%) | Water To hydrolysis zone (kg/h) | Water To washing zone (kg/h) |
|---|---|---|---|---|---|---|---|---|---|---|
| 1 | 48.3 | 0.382 | 48.3 | Na₂CO₃ | 22.3 | 0.210 | 10 | 10.9 | 183 | 60 |
| 2 | 48.3 | 0.382 | 48.3 | " | 20.2 | 0.191 | 0 | 11.2 | 160 | 60 |
| 3 | 48.3 | 0.382 | 48.3 | " | 22.3 | 0.210 | 10 | 10.9 | 183 | 60 |
| 4 | 96.6 | 0.763 | 96.6 | NaOH | 30.5 | 0.763 | 0 | 10.3 | 265 | 80 |
| 5 | 48.3 | 0.382 | 48.3 | NaHCO₃ | 35.3 | 0.420 | 10 | 14.2 | 214 | 60 |

| Ex. No. | Hydrolysis temp. (°C) | Hydrolysis pressure (bar) | Conversion (% of charged benzyl chloride) | Dibenzyl ether produced (% by weight of produced benzyl alcohol) | Raw product with toluene to first distillation column (kg/h) | First Product (kg/h) | Second Product (kg/h) |
|---|---|---|---|---|---|---|---|
| 1 | 145 | 18 | 99.90 | 0.55 | 90.7 | 41.0 | 40.5 |
| 2 | 145 | 27 | 99.01 | 0.55 | 90.7 | 41.1 | 40.6 |
| 3 | 125 | 12 | 99.70 | 0.40 | 90.8 | 41.1 | 40.7 |
| 4 | 145 | 8 | 99.99 | 5.80 | 180 | 72.6 | 72.5 |
| 5 | 125 | 16 | 99.80 | 0.35 | 90.7 | 41.0 | 40.7 |

TABLE 2

RAW MATERIAL CONSUMPTION PER KG BENZYL ALCOHOL

| Ex. No. | First Product Benzyl chloride kg/kg | First Product Hydr. agent kg/kg | Second Product Benzyl chloride kg/kg | Second Product Hydr. agent kg/kg |
|---|---|---|---|---|
| 1 | 1.18 | 0.544 | 1.19 | 0.551 |
| 2 | 1.18 | 0.491 | 1.19 | 0.498 |
| 3 | 1.18 | 0.543 | 1.19 | 0.548 |
| 4 | — | — | 1.33 | 0.420 |
| 5 | 1.18 | 0.861 | 1.19 | 0.867 |

TABLE 3

ENERGY CONSUMPTION PER KG BENZYL ALCOHOL

| Ex. No. | First Product Reactor column (kWh/kg) | First Product Distillation (kWh/kg) | Second Product Reactor column (kWh/kg) | Second Product Distillation (kWh/kg) |
|---|---|---|---|---|
| 1 | 0.151 | 0.442 | 0.153 | 0.802 |
| 2 | 0.146 | 0.441 | 0.148 | 0.801 |
| 3 | 0.124 | 0.442 | 0.125 | 0.800 |
| 4 | — | — | 0.120 | 0.893 |
| 5 | 0.134 | 0.442 | 0.135 | 0.798 |

TABLE 4

| Ex. No. | Benzyl chloride (kg/h) | Benzyl chloride (kmol/h) | p-Xylene (kg/h) | Hydrolyzing agent Type | Amount (kg/h) | Amount (kmol/h) | Molar excess (%) | Concentration (%) | Water To hydrolysis zone (kg/h) | Water To washing zone (kg/h) |
|---|---|---|---|---|---|---|---|---|---|---|
| 6 | 48.3 | 0.382 | 48.3 | Na$_2$CO$_3$ | 20.2 | 0.191 | 0 | 11.2 | 160 | 60 |
| 7 | 48.3 | 0.382 | 48.3 | Na$_2$CO$_3$ | 22.3 | 0.210 | 10 | 10.9 | 183 | 60 |

| Ex. No. | Hydrolysis temp. (°C.) | Hydrolysis pressure (bar) | Conversion (% of charged benzyl chloride) | Dibenzyl ether produced (% by weight of produced benzyl alcohol) | Raw product with p-xylene to first distillation column (kg/h) | First Product (kg/h) | Second Product (kg/h) |
|---|---|---|---|---|---|---|---|
| 6 | 145 | 25 | 99.10 | 0.54 | 90.7 | 41.1 | 40.6 |
| 7 | 125 | 11 | 99.52 | 0.48 | 90.7 | 41.1 | 40.7 |

TABLE 5
RAW MATERIAL CONSUMPTION PER KG BENZYL ALCOHOL

| | First Product | | Second Product | |
|---|---|---|---|---|
| Ex. No. | Benzyl chloride kg/kg | Hydr. agent kg/kg | Benzyl chloride kg/kg | Hydr. agent kg/kg |
| 6 | 1.18 | 0.491 | 1.19 | 0.498 |
| 7 | 1.18 | 0.543 | 1.19 | 0.548 |

TABLE 6
ENERGY CONSUMPTION PER KG BENZYL ALCOHOL

| | First Product | | Second Product | |
|---|---|---|---|---|
| Ex. No. | Reactor column (kWh/kg) | Distillation (kWh/kg) | Reactor column (kWh/kg) | Distillation (kWh/kg) |
| 6 | 0.146 | 0.441 | 0.148 | 0.801 |
| 7 | 0.124 | 0.442 | 0.125 | 0.800 |

TABLE 7

| Ex. No. | Benzal chloride (kg/h) | Benzal chloride (kmol/h) | Toluene (kg/h) | Hydrolyzing agent Type | Amount (kg/h) | Amount (kmol/h) | Molar excess (%) | Concentration (%) | Water To hydrolysis zone (kg/h) | Water To washing zone (kg/h) |
|---|---|---|---|---|---|---|---|---|---|---|
| 8 | 44.8 | 0.278 | 54.8 | Na$_2$CO$_3$ | 32.4 | 0.306 | 10 | 10.9 | 265 | 80 |
| 9 | 44.8 | 0.278 | 54.8 | " | 32.4 | 0.306 | 10 | 8.6 | 343 | 120 |

| Ex. No. | Hydrolysis temp. (°C.) | Hydrolysis pressure (bar) | Conversion (% of charged benzal chloride) |
|---|---|---|---|
| 8 | 125 | 12 | 99.45 |
| 9 | 145 | 18 | 99.98 |

What we claim and desire to secure by Letters Patent is:

1. A continuous method for the hydrolysis of an α-chlorinated toluene compound selected from the group consisting of benzyl chloride and benzal chloride, said method comprising hydrolyzing said α-chlorinated toluene compound at a temperature of from 10°-180° C. and at a pressure sufficient to maintain the components in a liquid state, with an aqueous solution of a hydrolyzing agent selected from the group consisting of hydroxides, carbonates, and hydrogen carbonates of alkali metals and alkaline earth metals in at least a stoichiometric amount of the presence of an inert organic solvent selected from the group consisting of benzene, toluene, xylene, ethyl benzene, and mixtures thereof, said hydrolysis reaction being conducted in countercurrent, with an organic phase containing said α-chlorinated toluene compound and said inert organic solvent flowing in a hydrolysis zone countercurrently with an aqueous phase containing said aqueous solution of said hydrolyzing agent, extracting said aqueous phase, after passing said hydrolysis zone, with said inert organic solvent in an extraction zone, washing said organic phase, after passing said hydrolysis zone, with water in a washing zone, and separating the resulting products of hydrolysis in said organic phase from said organic phase by distillation.

2. Method as claimed in claim 1, characterized by conducting the hydrolysis at a temperature of 100°-180° C.

3. Method as claimed in claim 1, characterized by conducting the hydrolysis with sodium carbonate as hydrolyzing agent.

4. Method as claimed in claim 1, characterized in that the inert organic solvent is toluene.

5. Method as claimed in claim 1, characterized in that the organic phase forms the continuous phase in the hydrolysis zone and the washing zone.

6. Method as claimed in claim 1, characterized in that the aqueous phase forms the continuous phase in the extraction zone.

7. Method as claimed in claim 1, characterized by mixing the inert organic solvent from the extraction zone with the α-chlorinated toluene compound and passing the mixture of the inert organic solvent and the α-chlorinated toluene compound through the hydrolysis zone.

8. Method as claimed in claim 1, characterized by supplying the inert solvent from the extraction zone to the organic phase from the washing zone.

9. Method as claimed in claim 1, characterized by recovering the resulting product of hydrolysis by distillation in two stages.

* * * * *